United States Patent [19]

Simmons

[11] Patent Number: 4,910,347
[45] Date of Patent: Mar. 20, 1990

[54] CYCLOALIPHATIC ALDEHYDES AND PROCESS FOR THE PREPARATION THEREOF

[75] Inventor: Dana P. Simmons, Geneva, Switzerland

[73] Assignee: Firmenich SA, Geneva, Switzerland

[21] Appl. No.: 263,104

[22] Filed: Oct. 13, 1988

Related U.S. Application Data

[62] Division of Ser. No. 81,267, Aug. 3, 1987, Pat. No. 4,800,233.

[30] Foreign Application Priority Data

Aug. 6, 1986 [CH] Switzerland ............... 3154/86

[51] Int. Cl.$^4$ ............................................. C07C 47/42
[52] U.S. Cl. .................................... 568/447; 568/356; 568/420
[58] Field of Search .................. 568/447, 420, 356

[56] References Cited

U.S. PATENT DOCUMENTS 4,594,456 6/1986 Luederssen ............... 568/447
4,800,233 1/1989 Simmons .................... 568/447

FOREIGN PATENT DOCUMENTS 0118809 9/1984 European Pat. Off. ........... 568/420
1204407 1/1960 France .............................. 568/449

OTHER PUBLICATIONS

Botton, "Chemical Abstract", vol. 66(1), 1967, 2254-2255.
Corey and Tius, "1-Diphenylphosphonio-1-Methoxymethyllithium, A Useful Reagent for the Synthesis of Aldehydes from Hindered Ketones", 21 Tetrahedron Letters, pp. 3535-3538, (1980).
Heyl and Herr, "Progesterone from 3-Acetoxybisnor-5-Cholenaldehyde and 3-Ketobisnor-4--Cholenaldehyde", 72, J. Amer. Chem. Soc., p. 2617, (1950).
de Botton, "Recherches sur les methylcyclohexylaldehydes", 33, Bull. Soc. Chim. Fr., p. 2466, (1966).
Barbier, I., "Extension de cycles dans la serie hydroaromatique, Essais avec la 1,1,3-trimethyl-cyclohexylmethylamine-5", 23, Helv. Chim. Acta, 519, at 529, (1940).
Perrottet et al., "Sur les etats energetiques comparatits des noyaux azulenique et napthalenique", 23, Helv. Chim. Acta, 1260 at 1265, (1940).
Prelog et al., "Uber die beiden diastereomeren tetrahydro-jonane", 31, Helv. Chim. Acta., p. 417, (1948).
Bachli et al., "Reduktion von Dihydro-cyclogeraniumsaure zu Dihydro-cyclogeraniol bwz. Dihydro-cyclocitral und Darstellung von cis-Dihydro-jon on", 34, Helv. Chim. Acta, p. 1160, (1951).

*Primary Examiner*—Werren B. Lone
*Attorney, Agent, or Firm*—Pennie & Edmonds

[57] ABSTRACT

Racemic and optically active cycloaliphatic 2,2,6-trimethylcyclohexanecarboxyaldehyde, also known as dihydrocyclocitral, are prepared by a novel process consisting in the cyclization of enol esters of formula

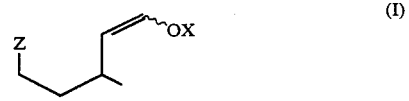

(I)

wherein the wavy line defines a C—O bond of cis or trans configuration, X represents an acyl group or P(O)-(OR)$_2$, wherein R stands for a lower alkyl monovalent radical or an aryl, and Z represents a monovalent radical of formula

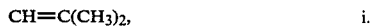

i.

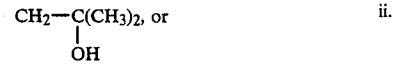

ii.

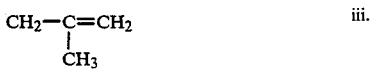

iii.

by means of an acid cyclization agent.

9 Claims, No Drawings

CYCLOALIPHATIC ALDEHYDES AND PROCESS FOR THE PREPARATION THEREOF

This is a division of application Ser. No. 081,267, filed Aug. 3, 1987, now U.S. Pat. No. 4,800,233.

BRIEF SUMMARY OF THE DISCLOSURE

The present invention relates to a process for the preparation of racemic and optically active dihydrocyclocitral, which process consists in cyclising by means of an acidic cyclisation agent an enol ester of formula

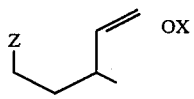
(I)

wherein the way line defines a C—O bond of cis or trans configuration, X represents an acyl group or P(O)-(OR)$_2$, wherein R stands for a lower alkyl monovalent radical or an aryl, and Z represents a monovalent radical of formula $CH=C(CH_3)_2$,    i.

$CH_2-C(CH_3)_2$, or    ii.
$\quad\ \ \ |$
$\quad\ \ \ OH$ $CH_2-C=CH_2$    iii.
$\quad\ \ \ |$
$\quad\ \ \ CH_3$

BACKGROUND OF THE INVENTION 2,2,6-Trimethyl-cyclohexanecarboxaldehyde, also known as dihydrocyclocitral, is a cycloaliphatic aldehyde of formula

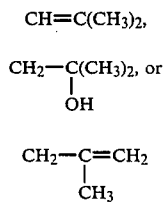
(III)

Not only does it represent a useful intermediate in a variety of organic syntheses but it constitutes a raw material for the preparation of useful end-products for the flavor and perfume industry as well as for the preparation of pharmaceuticals, namely for carotenoids and steroids type compounds (see in this respect European Patent Application No. 118,809 published on Sept. 19, 1984).

Numerous methods for its preparation have been described in the prior art.

M. de Bottom [Bull. Soc. Chim. de France, 33, 2466–73 (1966)] has described the preparation of dihydrocyclocitral starting from 2,2,6-trimethyl-cyclohexanone according to the following reaction scheme:

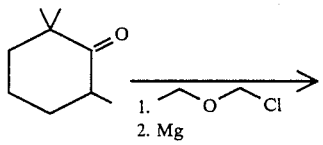

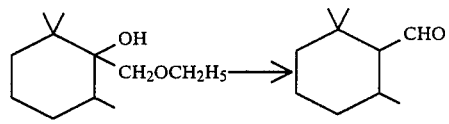

Earlier described methods are based on the hydrogenation of cyclocitral [Helv. Chim. Acta, 31, 417 (1948) and Helv. Chim. Acta, 34, 1160 (1951)] or on the oxidation of dihydrocyclogeraniol [Helv. Chim. Acta, 23, 529 (1940) and Helv. Chim. Acta, 23, 1265 (1940)]. The substitution of a ketonic oxygen atom by an hydrogen and a formyl group, a reaction of the type

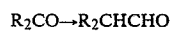
$R_2CO \rightarrow R_2CHCHO$ represents a useful approach in organic syntheses for which several specific reactants have been developed. However none of them gives satisfactory results in the case of the transformation of sterically hindered ketones having a hydrogen atom in the alpha position to the ketonic group. E. J. Corey and M. A. Tius [Tetrahedron Letters, 21, 3535-8 (1980)] have described a method for the preparation of dihydrocyclocitral starting from cyclohexanone, precisely by means of one of these specific reagents, diphenyl-methoxy-methyl phosphine. The nature of the reactant, however, renders the industrial scale-up application of this method rather problematic.

I have now discovered that dihydrocyclocitral could be obtained according to a simple and economical process, which process has the advantage of utilizing traditional reactants.

THE INVENTION

The instant invention relates to a process for the preparation of dihydrocyclocitral both in its racemic and optically active form, which process consists in the cyclisation by means of an acid cyclisation agent of an enol ester of formula (I).

Radical R, as defined above, represents a lower alkyl monovalent radical or an aryl. It can represent a $C_1$–$C_6$ alkyl radical, for example a methyl, an ethyl, a propyl or an isopropyl or a phenyl group. X represents an acyl group of the type R'CO, R' being preferably a lower alkyl radical having from 1 to 4 carbon atoms.

According to a preferred embodiment of the invention, the cyclisation is carried out on 3,7-dimethyl-octa-1,6-dien-yl acetate, on 3,7-dimethyl-7-hydroxy-oct-1-en-1-yl acetate or on 3,7-dimethyl-octa-1,7-dien-1-yl acetate. These esters, and the corresponding dialkyl- and diarylphosphate esters also defined by formula (I), can be obtained from citronellal or hydroxycitronellal according to a process analogous to prior described ones [see for example: J. Am. Chem. Soc. 72, 2617 (1950)]. For example, their preparation can be effected by treating citronellal or hydroxycitronellal with acetic anhydride in the presence of a basic reagent such as a tertiary amine, e.g. triethylamine, or in the presence of an alkali metal carbonate, for instance, potassium carbonate.

3,7-Dimethyl-octa-1,7-dien-1-yl acetate can be prepared by dehydration of hydroxycitronellal according to known techniques followed by esterification.

Acidic cyclisation agents include mineral or organic protonic acids or acids of Lewis type. Preferred cyclisation agents include sulphuric, phosphoric, polyphosphoric, methanesulfonic, acetic or trifluoroacetic acids, or, among the Lewis acids, tin tetrachloride, titanium tetrachloride or boron trifluoride, for example.

The temperature at which the cyclisation reaction is carried out is not critical and varies within a wide range of values. It is generally chosen as a function of the acidic agent utilized. Thus, good yields of end-products have been obtained by operating at 0° C. by using sulphuric acid as acidic agent and 3,7-dimethyl-octa-1,6-dien-1-yl diethylphosphate as starting ester. Good yields have been also obtained by treating 3,7-dimethyl-octa-1,6-dien-1-yl acetate with concentrated phosphoric acid or polyphosphoric acid at 100° C. Temperatures higher or lower than the above given limits can also be utilized.

Preferred embodiments of the present invention will be described in details in the specific examples of preparation.

As indicated above, the process of the invention possesses clear advantages over the prior known preparation methods with regard to the simplicity of the operations required and the overall economy. Besides, the process of the instant invention possesses the advantage of enabling for the first time the preparation of optically active dihydrocyclocitral, namely of the epimers of formula

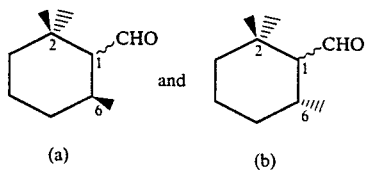

These two antipodes represent novel chemical entities, the preparation of which was not possible with the hitherto known processes.

Optically active dihydrocyclocitral derivativesd (a) and (b) represent useful starting materials for the preparation of optically active end-products, the interest of which lies in that their specific properties differ, to a lesser or greater extent, from those of their racemic counterpart. This is the case for a variety of biologically active compounds for which the physiological centers of reception in humans or animals are able to differentiate the specific nature of each of the perceived enantiomers, as this is the case, for instance, in olfactory perception.

In the present stage of our knowledge, there is no single theory able to elucidate the phenomenon of olfactor perception. However, experience has often shown that only one of the optically active forms of a given compound possesses the desired odorous fragrance properties, the racemate showing at best half of its odor intensity without however possessing the same olfactive character. On the other hand, the classical methods to resolve a racemate into its D and L components lead to a maximum of 50% of each of them. This renders the process highly unfavourable and the direct industrial pdreparation of pure antipodes represents therefore a major challenge.

Epimers (a) and (b) are obtained according to the process of the invention starting from optically active enol esters of formula (I). In fact, the cyclisation according to the invention occurs unexpectedly by complete retention of the configuration of the asymetric carbon atoms in position 6. Starting from (+)- or (−)-citronellal, it is thus possible to obtain the corresponding optically active enol ester immediates and subsequently enantiomeric dihydrocyclocitral.

(+)- and (−)-Citronellal represent active constituents in several essential oils from which they can be extracted. The two products are on the other hand available on the market at variable degree of purity. R(+)-citronellal can be obtained for instance from Chinese citronella accompanied by minor amounts of linalol and isopulegol.

The invention will be illustrated in the following examples wherein the temperatures are indicated in degrees centigrade and the abbreviations have the meaning common in the art.

EXAMPLE 1

(±)-Dihydrocyclocitral starting from (±)-citronellal a. 167 kg of acetic anhydride and 77 kg of potassium carbonate were heated to 80° in a reaction vessel equipped with an introduction pump and a condenser. 85 kg of (±)-citronellal were then added by means of the introduction pump during 40 min and the mixture was refluxed for 7 hours. After cooling, 100 kg of toluene and 500 l of water were added thereto and after separation of the organic phase the mixture was washed with 100 l of water to give a solution of 3,7-dimethyl-octa-1,6-dien-1-yl acetate in toluene accompanied by minor quantities of a diester of formula

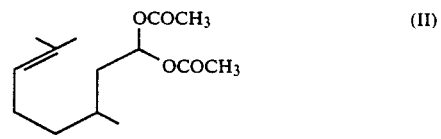

b. To the obtained solution, there were added 100 kg of toluene and 200 kg of 85% phosphoric acid and the resulting mixture was heated at 100° and stirred during 1 hour ¾ during which period the starting material had completely reacted. The reaction mixture was then cooled to 15° and 347 l of water were added. The organic phase was separated by decantation and washed with 100 l of a 6% aqueous solution of sodium bicarbonate while toluene was stripped off at a temperature of 60°–80°/150–110 mb. 91 kg of raw dihydrocyclocitral were thus obtained. The product was further purified by distillation on residue (57°–73°/30–9 mb). (±)-Dihydrocyclocitral was finally obtained in a 68.1% purity in a yield of 60.4% based on pure material (75.4 kg).

EXAMPLE 2

(±)-Dihydrocyclocitral starting from (±)-citronellal a. A mixture of 112.6 kg of acetic anhydride, 8.5 kg of potassium acetate and 56 kg of triethylamine was heated to 80° and, at this temperature, added of 84.5 kg of (±)-citronellal (addition time: 40 min). The mixture was kept refluxing for 7 hours and after cooling to room temperature, 100 kg of toluene and 350 l of water were added. The organic and water phase were then separated and the desired enol acetate accompanied by minor amounts of a diacetate of formula (II) was obtained as toluene solution.

b. The resulting solution was diluted by adding to it 100 kg of toluene and under stirring it was added of 200 kg of 85% phosphoric acid. The mixture was heated to 100° during 1 hour 40 min and, after cooling to 15°, it was added of 300 l of water while the organic phase was separated and washed with a 6% aqueous solution of sodium bicarbonate. Toluene was stripped off at reduced pressure (45°–88°/200–100 mb) to give 92.2 kg of raw (±)-dihydrocyclocitral. A distillation on residue (40°–60°/40–50 mb) has enabled to obtain 76.6 kg of (±)-dihydrocyclocitral of a purity of 65.7% (yield: 65.6% based on the pure material).

The following table summarizes the results obtained in the course of essays carried out by using other cyclisation acidic reagents.

| Example | X | Acid | Temp. [°C.] | Theor. yield [%] |
| --- | --- | --- | --- | --- |
| 3 | —P(O)(OC$_2$H$_5$)$_2$ | H$_2$SO$_4$ | 0° | 60 |
| 4 | CH$_3$CO | H$_2$SO$_4$ | 0° | 35 |
| 5 | CH$_3$CO | CH$_3$SO$_3$H | 0° | 42 |
| 6 | CH$_3$CO | TiCl$_4$ | 0° | 33 |
| 7 | CH$_3$CO | BF$_3$.O(C$_2$H$_5$)$_2$ | 0° | 55 |
| 8 | CH$_3$CO | H$_3$PO$_4$ 85% | 100° | 74 |
| 9 | CH$_3$CO | PPA | 100° | 72 |
| 10 | CH$_3$CO | F$_3$CCO$_2$H | 80° | 40 |

EXAMPLE 11

(+)-Dihydrocyclocitral

A mixture of 100 g of (+)-citronellal having an alpha$^{20}_D$= +9.4°, 132.5 g of acetic anhydride, 65.6 g of triethylamine and 10 g of potassium acetate was heated to 120° for 6 hours. After cooling to room temperature, 230 g of toluene were added to the reaction mixture whereupon water and an aqueous sodium bicarbonate solution were added to it. The organic phase was separated and poured onto an aqueous solution of 85% phosphoric acid (230 g) and the whole was heated to 100° during 90 min. After cooling, the mixture was washed with water and with an aqueous bicarbonate solution and finally concentrated. Simple distillation gave 73.5 g of a product having a content of 87% of dihydrocyclocitral (76% trans, 11% cis), alpha$^{20}_D$= +0.04° (pure). A further purification by distillation on a Fischer type column gave a pure product whose content of transisomer was 93%; alpha$^{20}_D$= +0.05° (pure)

EXAMPLE 12

(−)-Dihydrocyclocitral

S(−)-citronellal, obtained by oxidation of S(−)-citronellol (origin: Fluka A. G. Buchs, Switzerland), was converted into (−)-dihydrocyclocitral according to a process identical to that described in above Example 11. The product obtained had an alpha$^{20}_D$= −0.06° (pure).

EXAMPLE 13

(±)-Dihydrocyclocitral starting from 3,7-dimethyl-oct-7-enal a. A mixture of 16 g (0.16 mole) of acetic anhydride (1.2 g of potassium acetate) and 7.8 g (0.078 mole) of triethylamine was added of 12 g (0.078 mole) of 3,7-dimethyl-oct-7-enal and was refluxed for 6 hours.

After cooling to room temperature, water and toluene (40 ml) were added and the two phases separated.

b. The organic phase was mixed with 30 g of 85% phosphoric acid and the mixture was refluxed for 2 hours.

After cooling to room temperature, water was added to the resulting mixture and the organic phase was separated, concentrated and bulb distilled (bath temperature: 150°/15°20 mb). 9.5 G of (±)-dihydrocyclocitral of 74% purity were thus obtained.

3,7-Dimethyl-oct-7-enal, used as starting material in the process described above, was prepared by dehydration of hydroxycitronellal by means of potassium hydrogen sulfate.

EXAMPLE 14

(±)-Dihydrocyclocitral starting from hydroxycitronellal

By carrying out the reaction as indicated in above Example 13, and by using the reactants and quantities indicated below, there were obtainedd 22.3 g of (γ)-dihydrocyclocitral of 63% purity.

| | |
| --- | --- |
| a. hydroxycitronellal | 25 g |
| triethylamine | 37 g |
| acetic anhydride | 75 g |
| potassium acetate | 2.5 g |
| b. 85% phosphoric acid | 60 g |

What I claim is:

1. Optically active stereoisomers of dihydrocyclocitral of formula

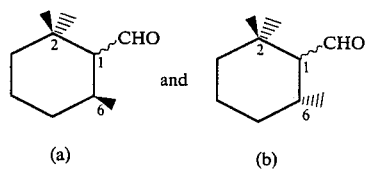

(a) and (b)

2. Optically active stereoisomers of dihydrocyclocitral having the formula

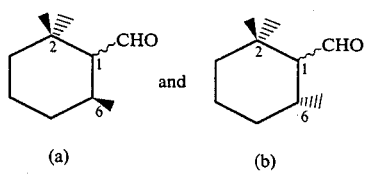

(a) and (b)

wherein said stereoisomers are produced by a process which comprises cyclizing by means of an acidic cyclization agent an enol ester having the formula

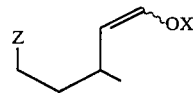

wherein the wavy line stands for a C—O bond of cis or trans configuration, X represents an acyl radical or P(O)(OR)$_2$, R is a lower alkyl monovalent radical or an aryl radical and Z represents a monovalent radical of the formula

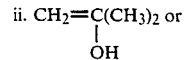

ii. CH$_2$=C(CH$_3$)$_2$ or

-continued iii. 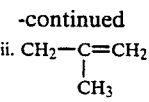

at a temperature and for a time enabling the formation of said stereoisomers.

3. The optically active stereoisomers of claim 2 wherein the enol ester is 3,7-dimethyl-octa-1,6-dien-1-yl acetate, 3,7-dimethyl-octa-1,7-dien-1-yl acetate or 3,7-dimethyl-7-hydroxy-oct-1-ene-1-yl acetate.

4. The optically active stereoisomers of claim 2 wherein the enol ester is 3,7-dimethyl-octa-1,6-dien-1-yl diethylphosphate, 3,7-dimethyl-octa-1,7-dien-1-yl diethylphosphate or 3,7-dimethyl-7-hydroxy-oct-1-en-1-yl diethylphosphate.

5. The optically active stereoisomers of claim 2 wherein the acidic cyclisation agent is a mineral or organic protonic acid or an acid of Lewis type.

6. The optically active stereoisomers of claim 5 wherein the acidic cyclisation agent is selected from among acetic acid, trifluoroacetic acid, phosphoric acid, methanesulfonic acid, boron trifluoride and titanium tetrachloride.

7. The optically active stereoisomers of claim 6 wherein the cyclisation is carried out at a temperature of between about 0° and 100° C.

8. The optically active stereoisomers of claim 2 wherein the enol ester is selected from enantiomers having the formula

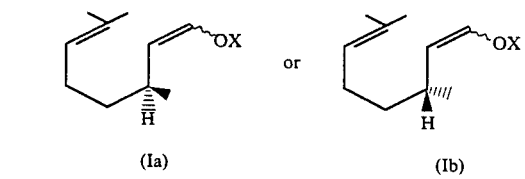

wherein the wavy line stands for a C—O bond of cis or trans configuration and X represents an aryl radical or P(O) (OR)$_2$ and wherein R is a lower alkyl monovalent radical or an aryl radical.

9. Optically active stereoisomers of dihydrocyclocitral having the formula

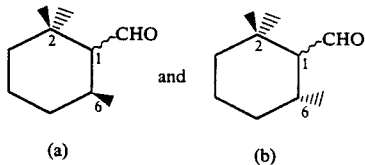

wherein said stereoisomers are produced by a process which comprises cyclizing by means of a mineral acid, organic acid or Lewis type acid an enol ester having the formula

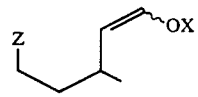

wherein the wavy line stands for a C—O bond of cis or trans configuration, X represents an acyl radical or P(O) (OR)$_2$, R is a lower alkyl monovalent radical or an aryl radical and Z represents a monovalent radical of the formula

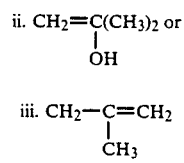

at a temperature of between about 0° and 100° C. and for a time enabling the formation of said stereoisomers.

* * * * *